US009560959B1

United States Patent
Hopkins et al.

(10) Patent No.: US 9,560,959 B1
(45) Date of Patent: Feb. 7, 2017

(54) CONTROL OF SCANNING IMAGES DURING VITREORETINAL SURGERY

(71) Applicant: NOVARTIS AG, Basel (CH)

(72) Inventors: Mark Hopkins, Lake Forest, CA (US); Robert Sanchez, Oceanside, CA (US); Ryan Takakawa, Lake Forest, CA (US); Lingfeng Yu, Rancho Santa Margarita, CA (US); Hugang Ren, Cypress, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/858,701

(22) Filed: Sep. 18, 2015

(51) Int. Cl.
| | |
|---|---|
| *A61B 3/14* | (2006.01) |
| *A61B 3/00* | (2006.01) |
| *A61B 3/13* | (2006.01) |
| *A61B 3/10* | (2006.01) |
| *A61F 9/007* | (2006.01) |

(52) U.S. Cl.
CPC .......... *A61B 3/0025* (2013.01); *A61B 3/0033* (2013.01); *A61B 3/0058* (2013.01); *A61B 3/102* (2013.01); *A61B 3/13* (2013.01); *A61B 90/20* (2016.02); *A61F 9/007* (2013.01)

(58) Field of Classification Search
USPC ................................................. 351/200–246
See application file for complete search history.

(56) References Cited

U.S. PATENT DOCUMENTS

| | | |
|---|---|---|
| 6,186,628 B1 | 2/2001 | Van De Velde |
| 2008/0015553 A1 | 1/2008 | Zacharias |
| 2011/0234977 A1 | 9/2011 | Verdooner |
| 2011/0304819 A1* | 12/2011 | Juhasz .................. A61B 3/102 351/206 |
| 2013/0116670 A1 | 5/2013 | Artsyukhovich et al. |
| 2016/0073868 A1* | 3/2016 | Raymond ............ A61B 3/0025 351/246 |

FOREIGN PATENT DOCUMENTS

WO     2014/106536     7/2014

OTHER PUBLICATIONS

International Search Report and Written Opinion of PCT Application No. PCT/IB2016/053954, mailed Sep. 26, 2016; 12 pages, Sep. 26, 2016.

* cited by examiner

*Primary Examiner* — Mohammed Hasan
(74) *Attorney, Agent, or Firm* — Baker Botts L.L.P.

(57) ABSTRACT

Control of scanning images during ophthalmic surgery may be performed with a scanning controller that interfaces to an optical scanner used with a surgical microscope. A scan control device may receive user input, including hands-free user input, for controlling an overlay image of scanning data that is overlaid on optical image data viewed using the surgical microscope. A selected location for optical scanning may also be displayed and controlled using the scanning controller.

22 Claims, 5 Drawing Sheets

CONTROL OF SCANNING IMAGES DURING VITREORETINAL SURGERY

BACKGROUND

Field of the Disclosure

The present disclosure relates to ophthalmic surgery, and more specifically, to control of scanning images during vitreoretinal surgery.

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus. For many types of vitreoretinal surgery using the surgical microscope, the surgeon may desire to have a very wide field of view of the fundus that extends beyond the equator and even out to the ora serrata. The optical system to provide the view of the fundus to the surgeon during vitreoretinal surgery may include a special ocular lens, of which three types are typically used: a direct (piano, flat, or magnifying) contact lens, an indirect non-contact lens, or an indirect contact lens.

In addition to viewing the fundus, many surgical microscopes may be equipped with optical scanners to provide additional information about portions of eye tissue involved with the vitreoretinal surgery. The optical scanners may be optically or electro-mechanically integrated into the surgical microscope. In typical system configurations, control of the optical scanner as well as viewing output images from the optical scanner are performed using different systems that a user, such as the surgeon, operates individually.

SUMMARY

The disclosed embodiments of the present disclosure provide for control of an optical scanner during vitreoretinal surgery, as well as viewing of output images from the optical scanner, that is integrated into the viewing display of a surgical microscope. In this manner, control of an optical scanner during vitreoretinal surgery, as described herein, may be performed by a surgeon using a single integrated field of view that includes optical images of the fundus, as well as output images from the optical scanner.

In one aspect, a disclosed method for performing ophthalmic surgery includes viewing an interior portion of an eye of a patient using a surgical microscope generating an optical image of the interior portion of the eye. The method may include, using a user input device, sending a first indication of a selected portion of the interior portion of the eye to a scanning controller coupled to an optical scanner. In the method, the scanning controller may be enabled to receive the first indication from the user input device, send a command to an optical scanner coupled to the surgical microscope to generate scan data for the selected portion, and receive the scan data from the optical scanner. In the method, based on the scan data, the scanning controller may further be enabled to generate an overlay image indicative of the scan data, generate a display element indicative of the selected portion, combine the display element and the overlay image with the optical image to generate a display image, and cause the surgical microscope to display the display image. In the method, the display element may be aligned with the selected portion in the optical image.

In any of the disclosed embodiments, the method may include, using the user input device, sending a second indication of a marker located within the selected portion to the scanning controller, while the scanning controller may be further enabled to receive the second indication from the user input device. Based on the second indication, the scanning controller may be enabled to add the marker to the display element and to the overlay image.

In any of the disclosed embodiments of the method, the display image may be output to at least one of: an oculus included with the surgical microscope, and an external display for the surgical microscope. In the method, the selected portion may be a line and the overlay image may correspond to a two-dimensional depth profile along the line. In any of the disclosed embodiments of the method, the selected portion may be an area and the overlay image may correspond to a three-dimensional depth profile over the area. In any of the disclosed embodiments of the method, the optical scanner may be an optical coherence tomography scanner.

In any of the disclosed embodiments of the method, the user input device may be a foot-operated device, while the first indication may be generated by a movement of the foot-operated device.

In any of the disclosed embodiments of the method, the user input device may be an audio device, while the first indication may be generated with a voice command received using the audio device.

In any of the disclosed embodiments of the method, the user input device may be a touch-sensitive device, while the first indication may be generated by touching the touch-sensitive device.

In any of the disclosed embodiments of the method, the user input device may be an optical scanning device, while the first indication may be generated with a gesture detected by the optical scanning device. In the method, the gesture may include motion by at least one of: a hand, a foot, a head, a surgical instrument, and an eye.

In another aspect, a disclosed scanning controller is for controlling scanning images during ophthalmic surgery. The scanning controller may be enabled to receive, from a user input device of a surgical microscope, a first indication of a selected portion of an interior portion of an eye of a patient, send a command to an optical scanner coupled to the surgical microscope to generate scan data for the selected portion, and receive the scan data from the optical scanner. The scanning controller may further be enabled to, based on the scan data, generate an overlay image indicative of the scan data, generate a display element indicative of the selected portion, combine the display element and the overlay image with an optical image generated by the surgical microscope to generate a display image, and cause the surgical microscope to display the display image. In the scanning controller, the display element may be aligned with the selected portion in the optical image.

In any of the disclosed embodiments, the scanning controller may be enabled to receive, from the user input device, a second indication of a marker located within the selected portion, and, based on the second indication, add the marker to the display element and to the overlay image.

In any of the disclosed embodiments of the scanning controller, the display image may be output to at least one of: an oculus included with the surgical microscope, and an external display for the surgical microscope.

In any of the disclosed embodiments of the scanning controller, the selected portion may be a line, while the overlay image may correspond to a two-dimensional depth profile along the line.

In any of the disclosed embodiments of the scanning controller, the selected portion may be an area, while the overlay image corresponds to a three-dimensional depth profile over the area.

In any of the disclosed embodiments of the scanning controller, the optical scanner may be an optical coherence tomography scanner.

In any of the disclosed embodiments of the scanning controller, the user input device may be a foot-operated device, while the first indication may be generated by a movement of the foot-operated device.

In any of the disclosed embodiments of the scanning controller, the user input device may be an audio device, while the first indication may be generated with a voice command received using the audio device.

In any of the disclosed embodiments of the scanning controller, the user input device may be a touch-sensitive device, while the first indication may be generated by touching the touch-sensitive device.

In any of the disclosed embodiments of the scanning controller, the user input device may be an optical scanning device, while the first indication may be generated with a gesture detected by the optical scanning device. In the scanning controller, the gesture may include motion by at least one of: a hand, a foot, a head, a surgical instrument, and an eye.

BRIEF DESCRIPTION OF THE DRAWINGS

For a more complete understanding of the present invention and its features and advantages, reference is now made to the following description, taken in conjunction with the accompanying drawings, in which.

DESCRIPTION OF PARTICULAR EMBODIMENT(S)

Figure 1:
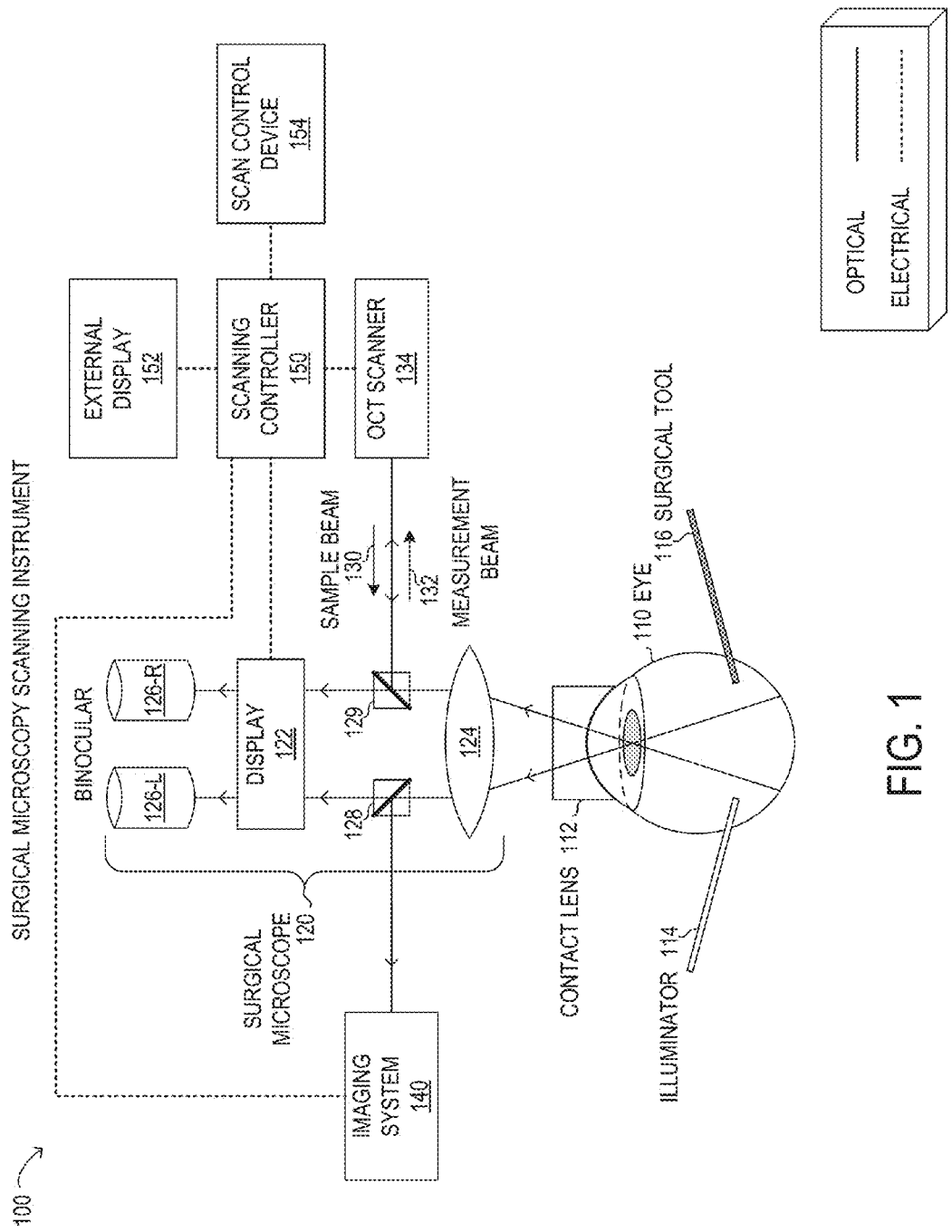
FIG. 1 is a block diagram of selected elements of an embodiment of a surgical microscopy scanning instrument.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during vitreoretinal surgery a surgeon may view the fundus of an eye of a patient using a surgical microscope, for example, in conjunction with a contact lens placed on the cornea. In order to perform any of a variety of surgical procedures, the surgeon may desire to optically scan certain portions of the fundus to generate profile depth scans of the corresponding eye tissue, such as by using an optical coherence tomography (OCT) scanner. The profile depth scans may reveal information about eye tissue that is not readily visible from optical images generated by the surgical microscope. Although optical scanners, such as OCT scanners, have been integrated with the optics of surgical microscopes, user operation of the resulting instrumentation may be unwieldy and impractical for use during vitreoretinal surgery. In particular, the surgeon may desire to spatially correlate the location of the optical scan, as well as scan data indicative of the profile depth scan, with the optical image from the surgical microscope, which may be difficult or time-consuming to perform during vitreoretinal surgery using different systems (i.e., the surgical microscope and the optical scanner) with independent operation and display outputs.

The present disclosure relates to control of scanning images during vitreoretinal surgery. The methods and systems for control of scanning images during vitreoretinal surgery disclosed herein may enable the surgeon to view scanning images of scan data in a single field of view of the optical images generated by the surgical microscope. The methods and systems for control of scanning images during vitreoretinal surgery disclosed herein may further enable the surgeon to control the location of a selected portion of the eye for scanning to generate the scanning images, and to view the selected portion in the single field of view. The methods and systems for control of scanning images during vitreoretinal surgery disclosed herein may enable the surgeon to set a marker within the selected location, and to view the marker at the displayed selected location and in the scanning images in the single field of view. The methods and systems for control of scanning images during vitreoretinal surgery disclosed herein may further enable the single field of view to be output to an external display. The methods and systems for control of scanning images during vitreoretinal surgery disclosed herein may enable the surgeon to provide user input using a foot-operated device, an audio device, a touch-sensitive device, an optical scanning device, or various combinations thereof.

As will be described in further detail, control of scanning images during vitreoretinal surgery is performed using a scanning controller that is integrated with the optical scanner and the surgical microscope. The scanning controller may send commands to control operation of the optical scanner, including for positioning of the optical scan and the selected location indicated by a user, typically the surgeon. The scanning controller may receive user input via a scan control device, which may be any one or more types of user input devices that enable hands-free operation, for example. Based on the user input and scan data received from the optical scanner, the scanning controller may update a display of the surgical microscope to show the selected location, as well as add an overlay image depicting the scan data. Additionally, the scanning controller may enable the user to set and place a marker that correlates a given position in the fundus with the scan data in the overlay image.

Referring now to the drawings, FIG. 1 is a block diagram showing a surgical microscopy scanning instrument 100. Instrument 100 is not drawn to scale but is a schematic representation. As will be described in further detail, instrument 100 may be used during vitreoretinal surgery to view and analyze a human eye 110. As shown, instrument 100 includes surgical microscope 120, scanning controller 150, external display 152, scan control device 154, and OCT scanner 134. Also shown in FIG. 1 are imaging system 140, contact lens 112, as well as surgical tool 116 and illuminator 114.

As shown, surgical microscope 120 is depicted in schematic form to illustrate optical functionality. It will be understood that surgical microscope 120 may include various other electronic and mechanical components, in different embodiments. Accordingly, objective 124 may represent a selectable objective to provide a desired magnification or field of view of the fundus. Objective 124 may receive light from the fundus of eye 110 via contact lens 112 that rests on a cornea of eye 110. It is noted that other types of lenses at eye 110 may be used with surgical microscope 120. To perform vitreoretinal surgery, various tools and instruments may be used, including tools that penetrate the sclera, represented by surgical tool 116. Illuminator 114 may be a special tool that provides a light source from within the fundus of eye 110.

In FIG. 1, surgical microscope 120 is shown with a binocular arrangement with two distinct but substantially equal light paths that enable viewing with binoculars 126 that comprise a left oculus 126-L and a right oculus 126-R. From objective 124, a left light beam may be split at beam splitter 128, from where imaging system 140 and left oculus 126-L receive the optical image. Also from objective 124, a right light beam may be split at partial mirror 129, which also receives sample beam 130 from OCT scanner 134, and outputs measurement beam 132 to OCT scanner 134. Partial mirror 129 also directs a portion of the right light beam to right oculus 126-R. Display 122 may represent an optoelectronic component, such as an image processing system that receives the data from scanning controller 150 and generates image output for left oculus 126-L and right oculus 126-R, respectively. In some embodiments, display 122 includes miniature display devices that output images to binoculars 126 for viewing by the user.

In FIG. 1, scanning controller 150 may have an electrical interface with display 122, for example, for outputting display data. In this manner, scanning controller 150 may output a display image to display 122 that is viewed at binoculars 126. Because the electrical interface between imaging system 140 and scanning controller 150 may support digital image data, scanning controller 150 may perform image processing in real-time with relatively high frame refresh rates, such that a user of surgical microscope 120 may experience substantially instantaneous feedback to user input for controlling the selected portion of eye 110 for scanning, as well as other operations. External display 152 may output similar images as display 122, but may represent a stand-alone monitor for viewing by various personnel during vitreoretinal surgery. Display 122 or external display 152 may be implemented as a liquid crystal display screen, a computer monitor, a television or the like. Display 122 or external display 152 may comply with a display standard for the corresponding type of display, such as video graphics array (VGA), extended graphics array (XGA), digital visual interface (DVI), high-definition multimedia interface (HDMI), etc.

With the binocular arrangement of surgical microscope 120 in FIG. 1, imaging system 140 may receive a portion of the left light beam that enables imaging system 140 to independently process, display, store, and otherwise manipulate light beams and image data. Accordingly, imaging system 140 may represent any of a variety of different kinds of imaging systems, as desired.

As shown, OCT scanner 134 may represent an embodiment of an optical scanner. It is noted that other types of optical scanners may be used with the arrangement depicted in FIG. 1. OCT scanner 134 may control output of sample beam 130 and may receive measurement beam 132 that is reflected back in response to photons of sample beam 130 interacting with tissue in eye 110. OCT scanner 134 may also be enabled to move sample beam 130 to the selected location indicated by the user. Scanning controller 150 may interface with OCT scanner 134, for example, to send commands to OCT scanner 134 indicating the selected location to generate scan data, and to receive the scan data from OCT scanner 134. It is noted that OCT scanner 134 may represent various types of OCT instruments and configurations, as desired, such as but not limited to time domain OCT (TD-OCT) and frequency domain OCT (FD-OCT). In particular, the scan data generated by OCT scanner 134 may include two-dimensional (2D) scan data of a line scan and three-dimensional (3D) scan data for an area scan. The scan data may represent a depth profile of the scanned tissue that enables imaging below a visible surface within the fundus of eye 110.

As shown, scan control device 154 represents any of a variety of devices and systems to provide user input. In various embodiments, certain functionality associated with scan control device 154 may be integrated within scanning controller 150, such as a device interface and executable code for device functionality. Furthermore, in some embodiments, at least a portion of scan control device 154 may be integrated within surgical microscope 120. As noted above, scan control device 154 may include a foot-operated device, an audio device, a touch-sensitive device, an optical scanning device, or various combinations thereof. A foot-operated device may be a joy stick or a trackball or a touch-sensitive device that enables the user to use a foot to provide user input. An audio device may be a microphone that is enabled to receive and identify voice commands. A touch-sensitive device may include a touch screen to respond to touch events, which may be operated using various body parts. An optical scanning device may detect images of the users body and interpret movements or gestures as input commands. For example, a scan control device may capture images of a movement of the user's hand, foot, head, eyes, or a surgical instrument controlled by the user, as nonlimiting examples. Scan control device 154 may be enabled to receive specific user input commands relating to positioning and defining the selected location for generating scan data.

The user input commands may accordingly include movement commands, size commands, rotation commands, among others. The user input commands may also be used to place and move a marker within the scan data, as described herein.

In operation of instrument 100, the user may view the fundus of eye 110 using binoculars while vitreoretinal surgery is performed on eye 110. The user may provide user input, such as in a hands-free manner, to scan control device 154 to operate OCT scanner 134. For example, the user input may include a first indication of a selected location within the field of view for generating scan data. Scanning controller 150 may then receive the first indication from scan control device 154 and send a command to OCT scanner 134 to generate scan data for the selected location that corresponds to a selected portion of the interior portion of eye 110. Scanning controller 150 may then receive the scan data from OCT scanner 134 and generate an overlay image indicative of the scan data. Scanning controller 150 may then overlay the overlay image on an optical image captured by surgical microscope 120 that is received from display 122. Scanning controller 150 may further overlay a display element indicative of the selected portion of eye 110 in alignment with the selected portion on the optical image. The user may provide additional user input, such as a location of a marker within the selected portion, using scan control device 154. Responsive to receiving a second indication of the marker from scan control device 154, scanning controller 150 may overlay, or add, the marker to the display element and the overlay image at corresponding locations. In this manner, the display image viewed by the user at binocular 126 includes the most recent updated information with regard to optical scanning.

Modifications, additions, or omissions may be made to surgical microscopy scanning instrument 100 without departing from the scope of the disclosure. The components and elements of surgical microscopy scanning instrument 100, as described herein, may be integrated or separated according to particular applications. Surgical microscopy scanning instrument 100 may be implemented using more, fewer, or different components in some embodiments.

Figure 2:
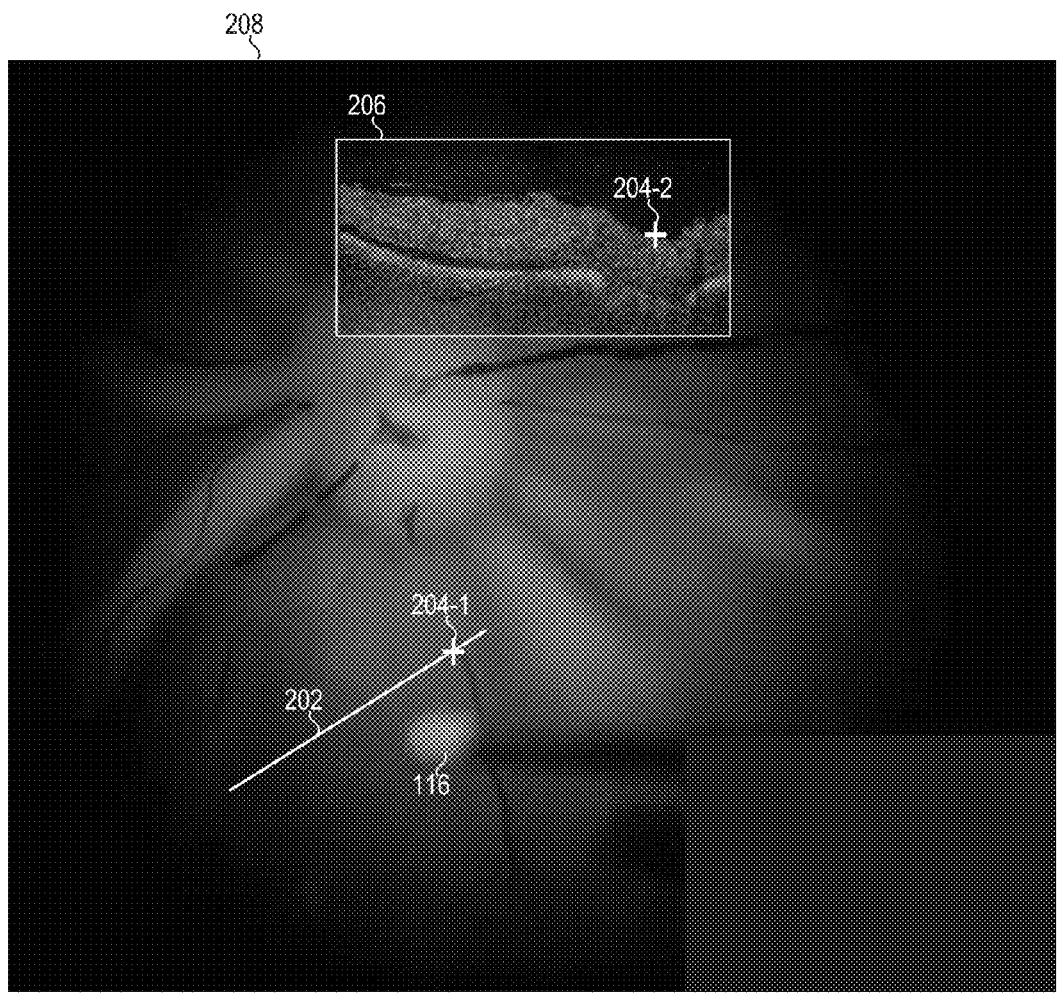
FIG. 2 is an embodiment of a surgical microscopy display image.

FIG. 2 shows an embodiment of a surgical microscopy display image 200. Display image 200 may represent a field of view seen by the user operating surgical microscopy scanning instrument 100 (see FIG. 1). As shown, display image 200 includes optical image 208 that is generated by surgical microscope 120. Optical image 208 may include a view of the fundus of eye 110, and may show certain surgical tools or instruments. In FIG. 2, surgical tool 116 is visible in the fundus in optical image 208. In addition to optical image 208, display image 200 includes additional elements that are overlaid onto optical image 208 during operation of instrument 100, as described previously. Specifically, a display element 202 is indicative of the selected portion at a location in the fundus where a line scan for optical scanning has been chosen by the user, using scan control device 154. Additionally, overlay image 206 shows scan data in the form of a 2D depth profile image corresponding to display element 202. Furthermore, marker 204 also shows a specific location that the user can select using scan control device 154. Marker 204 may be limited to a position along the line scan specified by display element 202. Marker 204-1 shows the marked location on display element 202, while marker 204-2 shows the corresponding marked location on overlay image 206. Although marker 204 is shown as a cross, various different types of shapes, lines, and points of various sizes and colors may be used for marker 204 in other embodiments.

Although a 2D line scan is shown in FIG. 2 for descriptive clarity, it will be understood that display element 202 may be a 2D area, while overlay image 206 depicts 3D scan data. Further control of display image 200 and elements therein may be performed by the user using scan control device 154. For example, a location or size of overlay image 206 may be selected or modified. Additionally, in some embodiments, scan control device 154 may be used to configure the optical scanner and to set certain optical scanning parameters.

Figure 3:
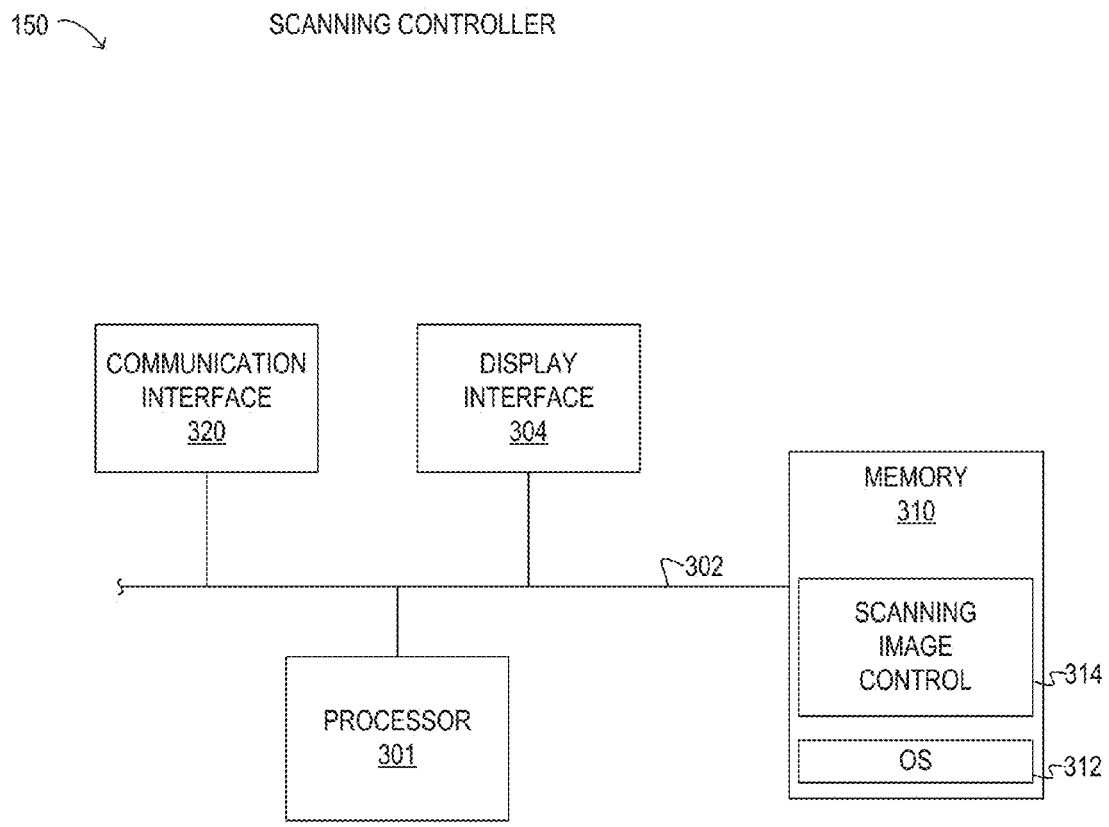
FIG. 3 is a block diagram of selected elements of an embodiment of a scanning controller.

Referring now to FIG. 3, a block diagram illustrating selected elements of an embodiment of scanning controller 150, described above with respect to FIG. 1, is presented. In the embodiment depicted in FIG. 3, scanning controller 150 includes processor 301 coupled via shared bus 302 to memory media collectively identified as memory 310.

Scanning controller 150, as depicted in FIG. 3, further includes communication interface 320 that can interface scanning controller 150 to various external entities, such as OCT scanner 134 or scan control device 154. In some embodiments, communication interface 320 is operable to enable scanning controller 150 to connect to a network (not shown in FIG. 3). In embodiments suitable for control of scanning images during vitreoretinal surgery, scanning controller 150, as depicted in FIG. 3, includes display interface 304 that connects shared bus 302, or another bus, with an output port for one or more displays, such as display 122 or external display 152.

In FIG. 3, memory 310 encompasses persistent and volatile media, fixed and removable media, and magnetic and semiconductor media. Memory 310 is operable to store instructions, data, or both. Memory 310 as shown includes sets or sequences of instructions, namely, an operating system 312, and a scanning image control application 314. Operating system 312 may be a UNIX or UNIX-like operating system, a Windows® family operating system, or another suitable operating system.

Figure 4:
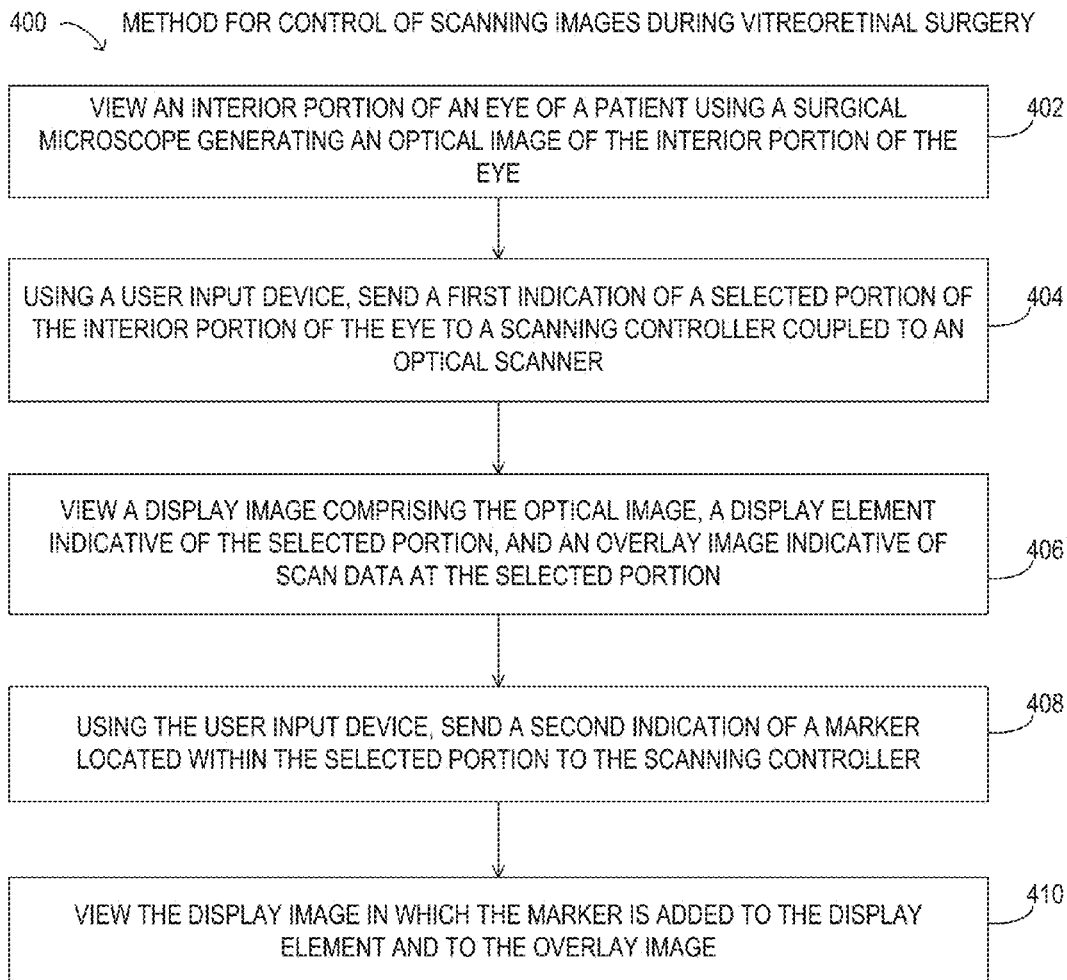
FIG. 4 is a flow chart of selected elements of a method for control of scanning images during vitreoretinal surgery.

Referring now to FIG. 4, a flow chart of selected elements of an embodiment of a method 400 for control of scanning images during vitreoretinal surgery, as described herein, is depicted in flowchart form. Method 400 describes steps and procedures that the user may perform while operating surgical microscopy scanning instrument 100 to view the fundus of an eye and performing surgical procedures based on the view of the fundus. It is noted that certain operations described in method 400 may be optional or may be rearranged in different embodiments. Method 400 may be performed by a surgeon or by other medical personnel. In some embodiments, at least certain portions of method 400 may be automated, for example using servo-mechanical control associated with certain aspects of the surgical microscope, such as raising or lowering the surgical microscope.

Method 400 may begin, at step 402, by viewing an interior portion of an eye of a patient using a surgical microscope generating an optical image of the interior portion of the eye. At step 404, using a user input device, a first indication of a selected portion of the interior portion of the eye may be sent to a scanning controller coupled to an optical scanner. At step 406, a display image comprising the optical image, a display element indicative of the selected portion, and an overlay image indicative of scan data at the selected portion may be viewed. At step 408, using the user input device, a second indication of a marker located within the selected portion may be sent to the scanning controller. At step 410, the display image in which the marker is added to the display element and to the overlay image may be viewed.

Figure 5:
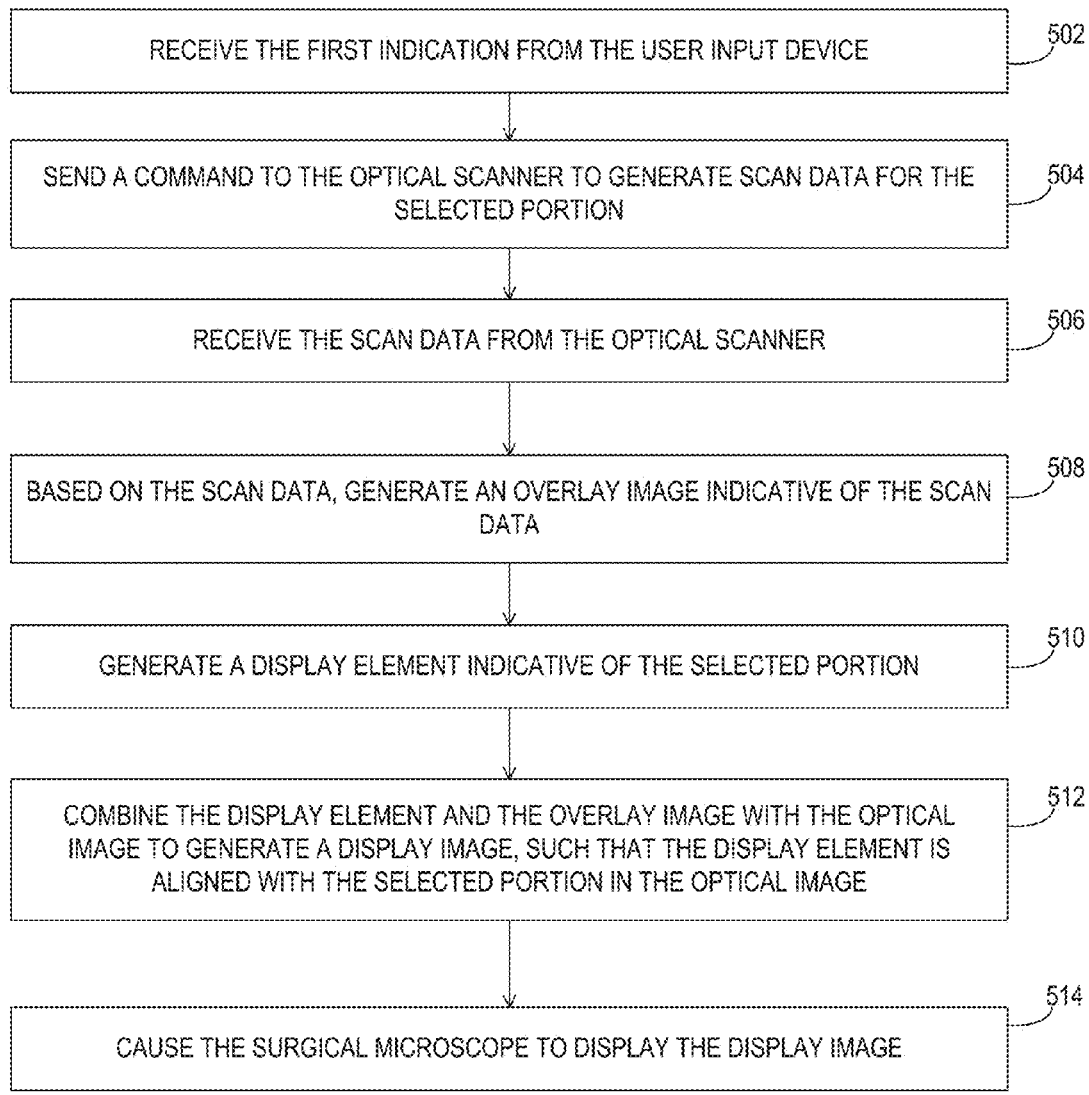
FIG. 5 is a flow chart of selected elements of a method for control of scanning images during vitreoretinal surgery.

Referring now to FIG. 5, a flow chart of selected elements of an embodiment of a method 500 for control of scanning images during vitreoretinal surgery, as described herein, is depicted in flowchart form. Method 500 describes steps and procedures that scanning controller 150 may perform while a user operates surgical microscopy scanning instrument 100 to view the fundus of an eye and performs surgical procedures based on the view of the fundus. Accordingly, at least certain portions of method 500 may be performed by scanning image control application 314. The user may be a surgeon or another medical personnel. It is noted that certain operations described in method 500 may be optional or may be rearranged in different embodiments. Method 500 may be performed in conjunction with method 400 in FIG. 4.

Method 500 may begin, at step 502, by receiving the first indication from the user input device. At step 504, a command may be sent to the optical scanner to generate scan data for the selected portion. At step 506, the scan data may be received from the optical scanner. Based on the scan data, at step 508, an overlay image indicative of the scan data may be generated. At step 510, a display element indicative of the selected portion may be generated. At step 512, the display element and the overlay image may be combined with the optical image to generate a display image, such that the display element is aligned with the selected portion in the optical image.

As disclosed herein, control of scanning images during ophthalmic surgery may be performed with a scanning controller that interfaces to an optical scanner used with a surgical microscope. A scan control device may receive user input, including hands-free user input, for controlling an overlay image of scanning data that is overlaid on optical image data viewed using the surgical microscope. A selected location for optical scanning may also be displayed and controlled using the scanning controller.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for performing ophthalmic surgery, the method comprising:
    viewing an interior portion of an eye of a patient using a surgical microscope generating an optical image of the interior portion of the eye;
    using a user input device, sending a first indication of a selected portion of the interior portion of the eye to a scanning controller coupled to an optical scanner, wherein the scanning controller is enabled to:
        receive the first indication from the user input device;
        send a command to an optical scanner coupled to the surgical microscope to generate scan data for the selected portion;
        receive the scan data from the optical scanner;
        based on the scan data, generate an overlay image indicative of the scan data;
        generate a display element indicative of the selected portion;
        combine the display element and the overlay image with the optical image to generate a display image, wherein the display element is aligned with the selected portion in the optical image; and
        cause the surgical microscope to display the display image.

2. The method of claim 1, further comprising:
    using the user input device, sending a second indication of a marker located within the selected portion to the scanning controller, wherein the scanning controller is further enabled to:
        receive the second indication from the user input device; and
        based on the second indication, add the marker to the display element and to the overlay image.

3. The method of claim 1, wherein the display image is output to at least one of: an oculus included with the surgical microscope; and an external display for the surgical microscope.

4. The method of claim 1, wherein the selected portion is a line and the overlay image corresponds to a two-dimensional depth profile along the line.

5. The method of claim 1, wherein the selected portion is an area and the overlay image corresponds to a three-dimensional depth profile over the area.

6. The method of claim 1, wherein the optical scanner is an optical coherence tomography scanner.

7. The method of claim 1, wherein the user input device is a foot-operated device, and the first indication is generated by a movement of the foot-operated device.

8. The method of claim 1, wherein the user input device is an audio device, and the first indication is generated with a voice command received using the audio device.

9. The method of claim 1, wherein the user input device is a touch-sensitive device, and the first indication is generated by touching the touch-sensitive device.

10. The method of claim 1, wherein the user input device is an optical scanning device, and the first indication is generated with a gesture detected by the optical scanning device.

11. The method of claim 10, wherein the gesture includes motion by at least one of: a hand, a foot, a head, a surgical instrument and an eye.

12. A scanning controller to control scanning images during ophthalmic surgery, the scanning controller enabled to:
    receive, from a user input device of a surgical microscope, a first indication of a selected portion of an interior portion of an eye of a patient;
    send a command to an optical scanner coupled to the surgical microscope to generate scan data for the selected portion;
    receive the scan data from the optical scanner;
    based on the scan data, generate an overlay image indicative of the scan data;
    generate a display element indicative of the selected portion;
    combine the display element and the overlay image with an optical image generated by the surgical microscope to generate a display image, wherein the display element is aligned with the selected portion in the optical image; and
    cause the surgical microscope to display the display image.

13. The scanning controller of claim 12, further enabled to:
    receive, from the user input device, a second indication of a marker located within the selected portion; and based on the second indication, add the marker to the display element and to the overlay image.

14. The scanning controller of claim 12, wherein the display image is output to at least one of: an oculus included with the surgical microscope; and an external display for the surgical microscope.

15. The scanning controller of claim 12, wherein the selected portion is a line and the overlay image corresponds to a two-dimensional depth profile along the line.

16. The scanning controller of claim 12, wherein the selected portion is an area and the overlay image corresponds to a three-dimensional depth profile over the area.

17. The scanning controller of claim 12, wherein the optical scanner is an optical coherence tomography scanner.

18. The scanning controller of claim 12, wherein the user input device is a foot-operated device, and the first indication is generated by a movement of the foot-operated device.

19. The scanning controller of claim 12, wherein the user input device is an audio device, and the first indication is generated with a voice command received using the audio device.

20. The scanning controller of claim 12, wherein the user input device is a touch-sensitive device, and the first indication is generated by touching the touch-sensitive device.

21. The scanning controller of claim 12, wherein the user input device is an optical scanning device, and the first indication is generated with a gesture detected by the optical scanning device.

22. The scanning controller of claim 21, wherein the gesture includes motion by at least one of: a hand, a foot, a head, a surgical instrument and an eye.

* * * * *